United States Patent [19]
Pasedach et al.

[11] 3,960,970
[45] June 1, 1976

[54] MANUFACTURE OF d.l-MENTHOL

[75] Inventors: Heinrich Pasedach, Ludwigshafen; Albrecht Friederang, Mannheim, both of Germany

[73] Assignee: BASF Aktiengesellschaft, Ludwigshafen, Germany

[22] Filed: Feb. 19, 1974

[21] Appl. No.: 443,412

[30] Foreign Application Priority Data
July 23, 1971 Germany..........................2136885
Jan. 27, 1972 Germany..........................2203807

Related U.S. Application Data

[62] Division of Ser. No. 272,147, July 17, 1972, Pat. No. 3,870,761.

Related U.S. Application Data

[62]

[52] U.S. Cl............................................. 260/631H
[51] Int. Cl............................................ C07C 35/12
[58] Field of Search................... 260/631 H; 272/147

[56] References Cited
UNITED STATES PATENTS

| | | | |
|---|---|---|---|
| 1,776,087 | 9/1941 | Blagden et al | 260/631 H |
| 1,811,777 | 6/1931 | Blagden | 260/631 H |
| 3,238,261 | 3/1966 | Beereboom | 260/587 |

OTHER PUBLICATIONS

Ueda, "Bull. Agr. Chem. Soc., Japan," Vol. 64, pp. 601–603 (1960).

*Primary Examiner*—David B. Springer
*Assistant Examiner*—Raymond V. Rush
*Attorney, Agent, or Firm*—Johnston, Keil, Thompson & Shurtleff

[57] ABSTRACT

Manufacture of piperitenone by mixing excess mesityl oxide with 10 to 70% by weight aqueous potassium hydroxide solution, heating the mixture to a temperature of between 20°C and the boiling point and introducing the methyl vinyl ketone into the heated mixture, *d,l*-methol is obtained directly, which is obtained in good yield.

1 Claim, No Drawings

MANUFACTURE OF D,L-METHOL

RELATED APPLICATION

This application is a division of our application Ser. No. 272,147, filed July 17, 1972, now U.S. Pat. No. 3,870,761, issued Mar. 11, 1975, the entire disclosure of which is herein incorporated.

The invention relates to an improved process for the manufacture of piperitenone by reaction of methyl vinyl ketone with excess mesityl oxide in the presence of basic catalysts.

It is known to manufacture piperitenone by reaction of mesityl oxide with methyl vinyl ketone in the presence of basic condensing agents.

Thus Bergman et al (J. Org. Chem., 24, 994 (1959)) describe a process in which sodium t-amylate is used as a basic condensing agent and toluene as the solvent and piperitenone is alleged to be obtained in a yield of 41% of theory. Later investigations by Naves et al (Bull. Soc. Chim. France, 1960, 378 and Compt. rend., 251, 1130 (1960)) however showed that the process of Bergmann et al mainly yields isoxylitone and only less than 8% of piperitenone.

Furthermore, J. J. Beereboom (U.S. Pat. No. 3,238,261 and J. Org. Chem., 31, 2026 (1966)) describes the reaction of methyl vinyl ketone with excess mesityl oxide in the presence of potassium hydroxide powder in tetrahydrofuran as the solvent. The piperitenone obtained is purified in a very expensive manner via the piperitenone-bisulfite adduct. In this process, yields of piperitenone of between 36 and 54% of theory are obtained.

A similar process is described by S. Ohshiro et al (Yakugaku Zasshi, 88, 417 (1968)). Here again the reaction of methyl vinyl ketone with excess mesityl oxide takes place in the presence of potassium hydroxide powder but without addition of tetrahydrofuran as the solvent. The piperitenone obtained is converted into a mixture of menthone and isomenthone by catalytic hydrogenation. However, in this process of yields of piperitenone are again only about 53%; furthermore, using this process the menthone/isomenthone mixture is obtained in only 64.6% yield and in a purity of only 89.8%. For this reason, the further reaction to give pure methol has to be carried out in an involved manner via menthone-oxime (Jap. Pat. No. 7,009,375) and menthylamine, which makes it doubtful whether the process is suitable for commercial operation.

It is an object of the invention to provide a process which enables piperitenone, and hence the mixture of menthone and isomenthone which can be manufactured therefrom by reduction, to be obtained in a simple manner, in better yields and higher purity.

We have found that the process for the manufacture of piperitenone by reaction of methyl vinyl ketone with mesityl oxide in the presence of a basic catalyst, in which methyl vinyl ketone is slowly introduced into excess mesityl oxide, may be carried out particularly advantageously by mixing excess mesityl oxide with 10 to 70% w/w aqueous potassium hydroxide solution, heating the mixture to a temperature of between 20°C and the reflux temperature (approx. 100°C), preferably between 50°C and the reflux temperature, and introducing the methyl vinyl ketone into the heated mixture.

According to a particularly simple embodiment of the invention, crude methyl vinyl ketone, as is obtained from 3-keto-1-butanol in known manner by splitting off water with acid, for example oxalic acid, is used. Instead of pure 3-keto-1-butanol it is possible to use, for example, the crude product from the thermal condensation of acetone with formaldehyde (see German Pat. No. 1,277,235), that is to say, a keto-butanol which contains impurities and major amounts of water. If, for example, 50 per cent strength aqueous keto-butanol is heated to the boil with oxalic acid, a methyl vinyl ketone/water azeotrope is continuously distilled off and fresh 50 per cent keto-butanol is added, an 80 to 85 per cent strength aqueous methyl vinyl ketone is obtained which can be used directly for the reaction according to the invention. In that case, admittedly, it is necessary to ensure that in the reaction with mesityl oxide the amount of water introduced with the methyl vinyl ketone is removed from the system by distillation.

It is surprising that the reaction of methyl vinyl ketone with excess mesityl oxide in the presence of aqueous potassium hydroxide solution and using methyl vinyl ketone/water mixtures should take place with far higher yields than could be expected from the known processes, especially since Beereboom in U.S. Pat. No. 3,238,261 states that better yields are obtained if the tetrahydrofuran used as the solvent is dried before the reaction, which means that the presence of water in the reaction mixture was regarded to be disadvantageous.

Usually, mesityl oxide condenses in the presence of bases to give isoxylitones (Furth and Wiemann, Bull. Soc. Chim. Fr., 1965, 1819), a reaction which takes place particularly readily at elevated temperature. It was not to be foreseen that this undesired side-reaction would be strongly repressed by the presence of water whilst the condensation of the mesityl oxide with methyl vinyl ketone to give piperitenone is favorably influenced.

The amount and concentration of the potassium hydroxide solution used and the reaction temperature can be varied within wide limits but in order to achieve particularly good yields it proves necessary to use more dilute solutions at high temperatures and more concentrated solutions at lower temperatures. For example, a concentration of 40 to 60% is advantageously used at a temperature of 50°–80°C. A particularly important feature for commercial operation is that the reaction can also be carried out at the reflux temperature (approx. 100°C). At temperatures of between about 80°C and the reflux temperature the aqueous potassium hydroxide solution is advantageously used in a concentration of 20 to 40%, preferably of 25 to 35%.

The potassium hydroxide is generally used in amounts of 0.05 mole to 1.5 mole, preferably of 0.1 mole to 0.7 mole, per mole of methyl vinyl ketone; if larger amounts of alkali are used, there is increased formation of by-products.

Instead of potassium hydroxide solution, aqueous sodium hydroxide solution can be used (compare example 17); the yields are however much lower and more by-products result.

At one and the same temperature, more undesired by-products are formed when using more concentrated alkalis whilst when using more dilute alkalis the yield diminishes.

A further advantageous embodiment of the present process consists in after-treating the crude piperitenone, preferably after neutralization and distillation with potassium hydroxide solution, for approx. half to 30 hours at about 20° to 80°C, preferably 40° to 50°C. If the crude piperitenone is after-treated as a distillate, potassium hydroxide powder is conveniently used. It is, however, also possible, as in the after-treatment of the reaction product which has not been distilled, to employ an aqueous potassium hydroxide solution of approx. 20 to 60 per cent strength. This results in a further increase in yield to above 80% of theory.

Mesityl oxide is used in an excess of 5 to 10 moles, preferably of about 10 moles, per mole of methyl vinyl ketone and serves as the sole solvent.

To carry out the process, the reactive methyl vinyl ketone is slowly added to the heated mixture of excess mesityl oxide and the alkali solution in a period of, generally, 10 minutes to several hours, preferably 30 to 60 minutes. If the reaction is carried out at relatively low temperature it is advisable to keep the reaction batch, after completion of the addition of the methyl vinyl ketone, for some time longer, that is to say up to approx. 30 hours, at the reaction temperature. If, on the other hand, the reaction is carried out at a higher temperature, especially at the reflux temperature, only a relatively short after-treatment is necessary.

Because of the known tendency of mesityl oxide to form isoxylitones under the action of alkali and because of the reactivity of the methyl vinyl ketone it appeared desirable to carry out the reaction at a low temperature, especially since it is stated in U.S. Pat. No. 3,238,261 that temperatures of above 30°C offer no advantages and frequently lead to reduced yields of piperitenone. It was therefore surprising that higher yields of piperitenone are obtained if, in accordance with the invention, the entire reaction is carried out at an elevated temperature, especially at the reflux temperature, that is to say if the method of the known processes of first bringing the methyl vinyl ketone into contact with the mesityl oxide and the alkali catalyst whilst cooling intensely and only then raising the temperature, which makes commercial operation of the process difficult, is not followed.

The correct balancing of the alkali concentration and the reaction temperature is of decisive importance as regards the yields of piperitenone and its purity. Most expediently, the process is carried out at the reflux temperature and with a 25 to 35% potassium hydroxide solution. When using commercially available 50% strength potassium hydroxide solution, the optimum reaction temperature is 60° to 70°C; even at a reaction temperature of 80°C the proportion of by-products is appreciably higher whilst at 50°C the yields obtained are less.

After completion of the reaction, the reaction mixture is neutralized with an inorganic or organic acid, preferably with formic acid, acetic acid or oxalic acid, and the organic phase is distilled. The excess mesityl oxide is thereby recovered in a simple manner.

The yield of crude piperitenone depends on the quality of the mesityl oxide employed. Since mesityl oxide is used in large excess, a possible water content of the mesityl oxide can have an effect on the concentration of the alkali hydroxide solution and hence on the yield of piperitenone. In such cases it is advisable to use a more concentrated aqueous solution so that the concentration of the solution present during the reaction lies within the abovementioned limits.

Using the process according to the invention, yields of 68 to 82% of piperitenone are obtained with technical mesityl oxide.

The crude piperitenone obtained is very difficult to purify by fractional distillation. It is much easier to remove the by-products if the crude piperitenone is hydrogenated to give a mixture of menthone and isomenthone and this mixture is subjected to fractional distillation. The reduction takes place in accordance with customary methods, for example by hydrogenation with palladium/active charcoal as the catalyst.

The present process for the manufacture of a menthone-isomenthone mixture offers substantial advantages over the known processes. The yield of piperitenone is 68 to 82% as compared to 53 or 54% in the known processes. Technical aqueous potassium hydroxide solution can be used as the condensing agent. Furthermore, an expensive solvent is not required; the excess mesityl oxide can be recovered simply and, as is shown by the examples, the process is extremely simple to carry out. On distilling the product obtained using potassium hydroxide powder as the condensing agent, Ohshiro et al obtained the menthone-isomenthone mixture in moderate yield and in a purity of only 89.8%, whilst in the present process a menthone-isomenthone mixture of 98% purity is obtained.

The purity achieved is of particular importance since the greatest part of the menthone-isomenthone mixture is used for the manufacture of menthol, for example by the method of Barney and Hass (Ind. Eng. Chem., 36, 85 (1944)), and the purity requirements of the methol used for pharmaceutical and cosmetic purposes are extremely high. It is also possible to hydrogenate the piperitenone directly to d,l-menthol. The hydrogenation of the crude piperitenone is carried out in accordance with methods customary for hydrogenations. Amongst the known hydrogenation catalysts, catalysts containing nickel have proved particularly suitable.

It is therefore particularly advantageous if in the hydrogenation of the piperitenone obtained to give the menthol isomer mixture, an unsupported catalyst which essentially contains nickel, or a catalyst which essentially contains nickel on a — preferably neutral or weakly basic — support, such as a magnesium silicate support, is used. Examples which may be mentioned are Raney nickel and nickel catalysts on silicates, containing magnesium, as the support to which optionally small amounts of molybdenum, copper and/or manganese have also been added.

The hydrogenation of the crude piperitenone is expediently carried out at temperatures at which as much d,l-menthol as possible is present in the menthol isomer mixture and no splitting off of water to form p-menthane takes place. Temperatures of 100° to 260°C, especially of 160° to 220°C, have proved advantageous.

The hydrogenation can be carried out batchwise or continuously.

To achieve good yields, it is advisable to employ hydrogen pressures of 50 to 300, preferably of 100 to 200, atmospheres gauge.

The reaction time is in general 5 to 30, preferably 12 to 24, hours.

From the mixture of substances formed in the hydrogenation of crude piperitenone it is possible, by fractional distillation, to isolate pure d,l-menthol in addition to the isomers neo-menthol, neo-iso-menthol and iso-menthol as well as the hydrogenated by-products of the piperitenone manufacture.

The isomers neo-menthol, neo-iso-menthol and isomenthol which arise during this distillation can, mixed with crude piperitenone, be converted into d,l-menthol under the hydrogenation conditions described above, or can, by themselves, be converted into d,l-menthol in a known manner.

Such an isomerization is described, for example, in German Pat. Nos. 489,819 and 493,268 and in French Pat. No. 1,547,530.

The mesityl oxide used for the examples which follow was a commercially available product containing 0.05% of water.

EXAMPLE 1

70 g of methyl vinyl ketone are added dropwise in the course of 30 minutes to 1,000 g of mesityl oxide and 55 ml of 30% potassium hydroxide solution whilst stirring at the reflux temperature (approx. 100°C). The mixture is neutralized with glacial acetic acid and the organic phase is distilled. The crude piperitenone (150 g) which passes over after distilling off the mesityl oxide up to 125°/15 mm Hg contains 68.8% of pipritenone; the yield of piperitenone is thus 68.8% relative to the amount of methyl vinyl ketone employed.

EXAMPLE 2

70 g of methyl vinyl ketone are added dropwise in the course of 60 minutes, whilst stirring, to 1,000 g of mesityl oxide and 50 ml of 50% potassium hydroxide solution, at 70°C. Thereafter the mixture is stirred for a further 10 minutes at 70°C and neutralized with glacial acetic acid, and the organic phase is distilled. 181 g of crude piperitenone are obtained; piperitenone content 55.7%, yield therefore 67.2%.

The examples which follow were carried out as in Example 2 with only the reaction temperature and the amount of KOH and concentration of KOH being changed in the way indicated.

| Ex. No. | Potassium Amount | Hydroxide Solution Concentration | Temp. | Distillate | Piperitenone Content | yield |
|---|---|---|---|---|---|---|
| 3 | 25 ml | 50% | 50°C | 152 g | 61.2% | 62.0% |
| 4 | 25 ml | 50% | 60°C | 173 g | 57.7% | 66.6% |
| 5 | 25 ml | 50% | 70°C | 183 g | 55.3% | 67.5% |
| 6 | 25 ml | 50% | 80°C | 222 g | 40.3% | 59.7% |
| 7 | 10 ml | 50% | 70°C | 195 g | 49.8% | 64.7% |
| 8 | 50 ml | 50% | 70°C | 181 g | 55.7% | 67.2% |
| 9 | 100 ml | 50% | 70°C | 180 g | 49.5% | 59.4% |
| 10 | 25 ml | 30% | 70°C | 135 g | 63.8% | 57.4% |
| 11 | 25 ml | 40% | 70°C | 147 g | 65.9% | 64.5% |
| 12 | 25 ml | 60% | 70°C | 210 g | 45.3% | 63.5% |
| 13 | 65 ml | 25% | reflux | 140 g | 67.0% | 62.7% |
| 14 | 55 ml | 30% | reflux | 148 g | 63.0% | 62.2% |

EXAMPLE 15

70 g of methyl vinyl ketone are added dropwise in the course of 60 minutes to 500 g of mesityl oxide and 25 ml of 50% strength potassium hydroxide solution at 70°, whilst stirring. Thereafter the mixture is worked up as in Example 2; 125 g of distillate containing 67.8% of piperitenone are obtained; yield 56.6%.

EXAMPLE 16 (comparative example)

70 g of methyl vinyl ketone are added dropwise in the course of 60 minutes at 20°C to 1,000 g of mesityl oxide and 20 g of potassium hydroxide powder. 175 g of distillate containing 34.6% of piperitenone are obtained; yield 40.4%.

EXAMPLE 17

70 g of methyl vinyl ketone are added dropwise in the course of 60 minutes at 70°C to 1,000 g of mesityl oxide and 25 ml of 50% sodium hydroxide solution. 183 g of distillate containing 37.5% of piperitenone are obtained; yield 45.8%.

EXAMPLE 18

200 g of crude piperitenone (piperitenone content: 63%) are dissolved in 100 ml of methanol and hydrogenated with 2 g of Pd/active charcoal (5% strength) at an excess hydrogen pressure of 200 mm water column, initially for 5 hours whilst cooling with ice and then for 48 hours at 25°C. The crude product is distilled through a 1 m packed column. 115 g of a fraction boiling at 101° to 103°/23 mm Hg and consisting of menthone/isomenthone in 98% purity are obtained.

EXAMPLE 19

10 ml of 50% potassium hydroxide solution are added in the course of 1 to 2 minutes to a mixture of 1,500 g of mesityl oxide and 0.5 g of hydroquinone which is boiling at approx. 114°C. 83 g of aqueous methyl vinyl ketone (containing 13 g of water) are then added dropwise in the course of 60 minutes and at the same time approx. 15 g of water are withdrawn from the condensate of mesityl oxide and water which separates out at the head of the column and separates into two layers.

The mixture is heated for a further 2 hours under reflux, and the reaction mixture is neutralized by adding 8 ml of formic acid and distilled. 156 g of crude piperitenone containing 75% of piperitenone (yield 78%) are obtained.

If this crude piperitenone, together with 5 ml of 50% potassium hydroxide solution, is stirred for 3 hours at 40° – 50°C, the piperitenone content rises to 79%, representing a total yield of piperitenone of 82%.

EXAMPLE 20

200 g of crude piperitenone (piperitenone content: 58.7%) are hydrogenated in an autoclave over 5 g of Raney nickel at 200°C and 150 atmospheres hydrogen pressure for 24 hours. After filtering off the catalyst, 184 g of a mixture containing 14.2% of neo-menthol, 16.2% of neo-iso-menthol, 14.4% of menthol and 19.4% of iso-menthol remain.

EXAMPLE 21

An 0.3 l hydrogenation reactor is filled with 0.2 l of a commercially available supported nickel catalyst (39.8% of Ni and 1.8% of Mo on magnesium silicate). The catalyst is first reduced with hydrogen at 270°C for 10 hours under normal pressure and then for 25 hours at a pressure which is increased stepwise to 200 atmospheres gauge. Thereafter, crude piperitenone containing 58.7% of piperitenone is pumped at a speed of 10 ml/hour upwardly through the reactor at 150 atmospheres hydrogen pressure. The table shows the composition of the resulting product as a function of the temperature.

| Reactor Temperature | p-Menthane % | Neo-Menthol % | Neo-Iso-Menthol % | Menthol % | Iso-Menthol % |
|---|---|---|---|---|---|
| 160°C | 1.3 | 16.1 | 3.7 | 37.1 | 13.9 |

-continued

| Reactor Temperature | p-Menthane % | Neo-Menthol % | Neo-Iso-Menthol % | Menthol % | Iso-Menthol % |
|---|---|---|---|---|---|
| 180°C | 1.3 | 16.1 | 4.6 | 35.7 | 14.7 |
| 200°C | 2.1 | 16.9 | 3.3 | 37.1 | 15.9 |
| 220°C | 3.3 | 16.7 | 3.2 | 35.5 | 14.1 |

EXAMPLE 22

4,165 g of a mixture obtained by hydrogenation of crude piperitenone are distilled through a column of 2 m length and 5 cm diameter, filled with 5 mm wire mesh rings, in a waterpump vacuum, using a reflux ratio of 25 and a through-put of 600 g/hour. The following fractions are obtained:

1. 398 g of by-products (boiling point 50° to 75°/20 mm);
2. 209 g containing about 50% of neo-menthol and about 50% of by-products (boiling point 75° to 109°/20 mm);
3. 1,171 g of a mixture of neo-menthol, neo-iso-menthol and menthol (boiling point 109°/20 mm);
4. 686 g of menthol (97.7% strength), solidification point (according to German Pharmacopoeia 7):29.4°C (boiling point 109°/20 mm);
5. 551 g of a mixture of menthol and iso-menthol (boiling point 109° to 110°/20 mm).

Renewed distillation of the menthol fraction yields a product of 99.9% purity, solidification point (according to German Pharmacopoeia 7): 31.4°C.

The invention is hereby claimed as follows:

1. In the process for manufacture of d,l-menthol wherein crude piperitenone prepared by reaction of methyl vinyl ketone with mesityl oxide in the presence of a basic catalyst, in which methyl vinyl ketone is slowly introduced into a mixture consisting essentially of excess mesityl oxide and, as the catalyst, 10 to 70% w/w aqueous potassium hydroxide solution, the mixture is brought to a temperature of between 20°C and the reflux temperature, the potassium hydroxide is used in an amount of 0.05 mole to 1.5 mole per mole of methyl vinyl ketone, and the methyl vinyl ketone is introduced into said mixture at said temperature, the steps which comprise hydrogenating the crude mixture of piperitenone and by-products so obtained in the presence of a nickel containing catalyst at a temperature of from 100° to 260°C to give a mixture of d,l-menthol, the menthol isomers neo-menthol, neo-iso-menthol and iso-menthol and hydrogenated by-products of the piperitenone manufacture, separating the resulting hydrogenated mixture by fractional distillation into d,l-menthol said menthol isomers and said hydrogenated by-products, and recovery substantially pure d,l-menthol.

2. A process as claimed in claim 1 wherein the catalytic hydrogenation of the crude piperitenone is carried out with an unsupported hydrogenation catalyst consisting essentially of nickel.

3. A process as claimed in claim 1 wherein the catalytic hydrogenation of the crude piperitenone is carried out with a hydrogenation catalyst consisting essentialy of nickel on a magnesium silicate support.

4. A process as claimed in claim 1 wherein the catalytic hydrogenation of the crude piperitenone is conducted at 160-220°C.

5. A process as claimed in claim 1, wherein the reaction of methyl vinyl ketone with mesityl oxide is carried out in the presence of 40 to 60% w/w aqueous potassium hydroxide solution and at a temperature of from 50° to 80°C.

6. A process as claimed in claim 1 wherein the reaction of methyl vinyl ketone with mesityl oxide is carried out in the presence of 20 to 40% w/w aqueous potassium hydroxide solution and at a temperature of between 80°C and the reflux temperature.

7. A process as claimed in claim 1, wherein the d,l-menthol fraction is redistilled to recover d,l-menthol of substantially 100% purity.

* * * * *

UNITED STATES PATENT AND TRADEMARK OFFICE
CERTIFICATE OF CORRECTION

PATENT NO. : 3,960,970
DATED : June 1, 1976
INVENTOR(S) : PASEDACH et al

It is certified that error appears in the above–identified patent and that said Letters Patent are hereby corrected as shown below:

In the Heading, delete "[54] MANUFACTURE OF d.1-MENTHOL " and substitute -- [54] MANUFACTURE OF D,L-MENTHOL --

In the Heading, delete " [62] Related U.S. Application Data " (second occurence)

In the Heading, delete

" [56]         References Cited         "

UNITED STATES PATENTS
| | | | |
|---|---|---|---|
| 1,776,087 | 9/1941 | Blagden et al | 260/631 H |
| 1,811,777 | 6/1931 | Blagden | 260/631 H |
| 3,238,261 | 3/1966 | Beereboom | 260/587 | and substitute

-- [56]         References Cited         --

UNITED STATES PATENTS
| | | | |
|---|---|---|---|
| 1,776,087 | 9/1930 | Schollkopf et al | 260/631 H |
| 1,811,777 | 8/1931 | Blagden | 260/631 H |
| 2,237,980 | 4/1941 | Blagden et al | 260/631 H |
| 3,238,261 | 3/1966 | Beereboom | 260/587 |

In the Abstract, delete " ... mixture, d,1-methol is obtained directly, which is obtained in good yield. " and substitute -- ... mixture. d,1-menthol is obtained directly, or via a

UNITED STATES PATENT OFFICE
CERTIFICATE OF CORRECTION

Patent No. 3,960,970          Dated June 1, 1976

Inventor(s) Pasedach et al

It is certified that error appears in the above-identified patent and that said Letters Patent are hereby corrected as shown below:

mixture of methone and isomenthone, from the piperitenone which is obtained in good yield. --

Signed and Sealed this

Eighth Day of March 1977

[SEAL]

Attest:

RUTH C. MASON
*Attesting Officer*

C. MARSHALL DANN
*Commissioner of Patents and Trademarks*